US012661007B2

(12) United States Patent
Li et al.

(10) Patent No.: US 12,661,007 B2
(45) Date of Patent: Jun. 23, 2026

(54) INTRAOCULAR PRESSURE SENSOR

(71) Applicant: Board of Trustees of Michigan State University, East Lansing, MI (US)

(72) Inventors: Wen Li, Okemos, MI (US); Arthur J. Weber, East Lansing, MI (US); Mohammad Hossein Mazaheri Kouhani, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 902 days.

(21) Appl. No.: 17/959,560

(22) Filed: Oct. 4, 2022

(65) Prior Publication Data

US 2023/0021626 A1 Jan. 26, 2023

Related U.S. Application Data

(62) Division of application No. 16/494,894, filed as application No. PCT/US2018/023502 on Mar. 21, 2018, now Pat. No. 11,484,202.

(60) Provisional application No. 62/474,750, filed on Mar. 22, 2017.

(51) Int. Cl.

| | |
|---|---|
| ***A61B 3/16*** | (2006.01) |
| ***A61B 5/00*** | (2006.01) |
| ***A61B 5/07*** | (2006.01) |
| ***G01L 9/00*** | (2006.01) |

(52) U.S. Cl.

CPC .................. *A61B 3/16* (2013.01); *A61B 5/07* (2013.01); *G01L 9/0004* (2013.01); *G01L 9/0005* (2013.01); *A61B 5/6832* (2013.01); *A61B 2562/0247* (2013.01)

(58) Field of Classification Search

CPC ........... A61B 3/16; A61B 5/07; A61B 5/6832; A61B 2562/0247; G01L 9/0004; G01L 9/0005; G01L 9/007; G01L 9/0072

See application file for complete search history.

(56) References Cited

U.S. PATENT DOCUMENTS

| | | | |
|---|---|---|---|
| 6,089,711 | A | 7/2000 | Blankenbecler et al. |
| 7,137,956 | B2 | 11/2006 | Leonardi et al. |

(Continued)

FOREIGN PATENT DOCUMENTS

| | | | |
|---|---|---|---|
| CN | 204218877 | U | 3/2015 |
| WO | WO-2014/184137 | A1 | 11/2014 |
| WO | WO-2016/071253 | A1 | 5/2016 |

OTHER PUBLICATIONS

Pan, C.T., et al., "Study of micro-lens array by reflow process," Journal of Modern Optics, vol. 55, No. 17, pp. 2843-2856 (Oct. 10, 2008).

(Continued)

*Primary Examiner* — Marlon T Fletcher
*Assistant Examiner* — Kimberly Newman Frey
(74) *Attorney, Agent, or Firm* — Harness, Dickey & Pierce, PLC

(57) ABSTRACT

A pressure sensor system is provided. In another aspect, a wireless intraocular pressure sensor includes a deformable or stretchable inductor. A further aspect of an intraocular pressure sensing system includes a deformable inductor sized to contact an eye. Another aspect provides an organ pressure sensing system including a passive inductor with a wavy, serpentine or undulating shape.

22 Claims, 8 Drawing Sheets

(56) References Cited

U.S. PATENT DOCUMENTS

| | | | | |
|---|---|---|---|---|
| 8,926,524 | B2 * | 1/2015 | Chen | A61B 5/031<br>600/398 |
| 9,271,677 | B2 | 3/2016 | Leonardi | |
| 11,484,202 | B2 | 11/2022 | Li et al. | |
| 11,497,399 | B2 * | 11/2022 | Adams | A61B 5/00 |
| 2009/0299216 | A1 | 12/2009 | Chen et al. | |
| 2010/0016704 | A1 | 1/2010 | Naber et al. | |
| 2012/0277568 | A1 | 11/2012 | Chiou et al. | |
| 2013/0184554 | A1 | 7/2013 | Elsheikh et al. | |
| 2014/0243645 | A1 | 8/2014 | Leonardi | |
| 2015/0073253 | A1 | 3/2015 | Bouwstra et al. | |
| 2015/0087953 | A1 | 3/2015 | Chiou et al. | |
| 2015/0173680 | A1 | 6/2015 | Etzkorn et al. | |
| 2016/0051143 | A1 | 2/2016 | Rickard et al. | |
| 2017/0040306 | A1 * | 2/2017 | Kim | H10W 90/00 |
| 2017/0127941 | A1 * | 5/2017 | Ostermeier | A61B 5/0031 |
| 2017/0280997 | A1 | 10/2017 | Lai et al. | |
| 2017/0336396 | A1 | 11/2017 | Yu et al. | |
| 2019/0021650 | A1 * | 1/2019 | Lee | A61B 5/0004 |
| 2019/0033653 | A1 * | 1/2019 | Cho | G02F 1/13439 |

OTHER PUBLICATIONS

Liu, C.F., et al., “Design and fabrication of double-sided optical film for OLED lighting,” Optics Communications 291, p. 349-358 (Nov. 13, 2012).

Fuh, Y.K., “Self-Powered Pressure Sensor with fully encapsulated 3D printed wavy substrate and highly-aligned piezoelectric fibers array,” Scientific Reports, 7:6759 (Jul. 28, 2017).

Dunbar, G.E., “The Sensimed Triggerfish contact lens sensor: efficacy, safety, and patient perspectives,” Clinical Ophthalmology, vol. 11, pp. 875-882 (May 8, 2017).

Chen, Po-Jui, et al.: “Implantable Micromechanical Parylene-Based Pressure Sensors for Unpowered Intraocular Pressure Sensing,” Journal of Micromechanics and Microengineering, 17, Aug. 31, 2007, pp. 1931-1938.

Chen, Po-Jui: “Implantable Wireless Intraocular Pressure Sensors,” Thesis—California Institute of Technology, 2009, 187 pages.

Crum, Brian, et al.: “Parlyene Based Fold-and-Bond Wireless Pressure Sensor,” Department of Electrical and Computer Engineering, IEEE, NEMS2013, Suzhou, China, Apr. 7-10, 2013, pp. 1155-1158.

Deffree, Suzanne: “Researchers Claim Millimeter Scale Computing System,” Pulse, EDN, Apr. 7, 2011, p. 12.

Dow Corning Product Information: Sylgard® 184 Silicone Elastomer, Apr. 2, 2014, four pages.

Katuri, Kalyan Chakravarthi: “Design and Optimization of Passive Wireless Intraocular Pressure Sensor,” Dissertation—North Carolina State University, 2012, 131 pages.

Leonardi, Matteo, et al.: “First Steps Toward Noninvasive Intraocular Pressure Monitoring With a Sensing Contact Lens,” Investigative Ophthalmology & Visual Science, vol. 45, No. 9, Sep. 2004, pp. 3113-3117.

MicroChem Nano™ PMMA and Copolymer Data Sheet, 2001, eight pages.

Sánchez, Irene, et al.: “Prototype of a Nanostructured Sensing Contact Lens for Noninvasive Intraocular Pressure Monitoring,” Investigative Ophthalmology & Visual Science, vol. 52, No. 11, Oct. 2011, pp. 8310-8315.

Specialty Coating Systems™ brochure, 2007, 12 pages.

Sigma-Aldrich® Product Specification: Poly(3,4-ethylenedioxythiopene)-poly(styrenesulfonate)—3.0-4.0% in H2O1 (high-conductivity grade), published prior to Mar. 2017, one page.

Supplementary European Search Report for EP 18 77 2211, dated Nov. 13, 2020.

Todani, Amit et al.: “Intraocular Pressure Measurement by Radio Wave Telemetry,” Investigative Ophthalmology & Visual Science, vol. 52, No. 13, Dec. 2011, pp. 9573-9580.

“Transponder System for Measuring and Monitoring the Intraocular Pressure,” Fraunhofer Institut Mikroelektronische Schaltungen und Systeme, published prior to Mar. 2017, two pages.

Yu, Lawrence, et al.: “Chronically Implanted Pressure Sensors: Challenges and State of the Field,” Sensors, ISSN 1424-8220, Oct. 31, 2014, pp. 20620-20644.

M. H. M. Kouhani, et al, “Wireless intraocular pressure sensor using stretchable variable inductor”, 2017 IEEE 30th International Conference on Micro Electro Mechanical Systems (MEMS), Las Vegas, NV (Feb. 28, 2017).

* cited by examiner

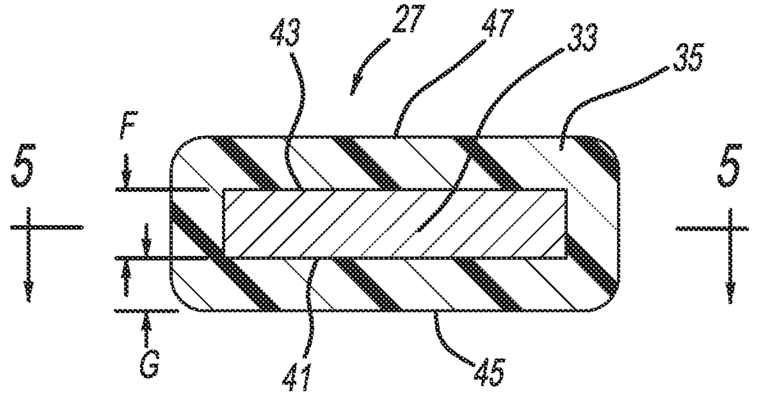
FIG - 3
FIG - 4
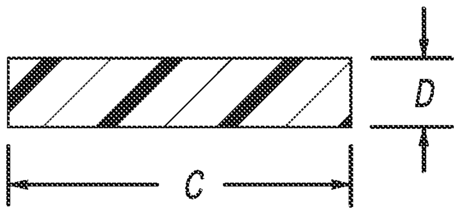
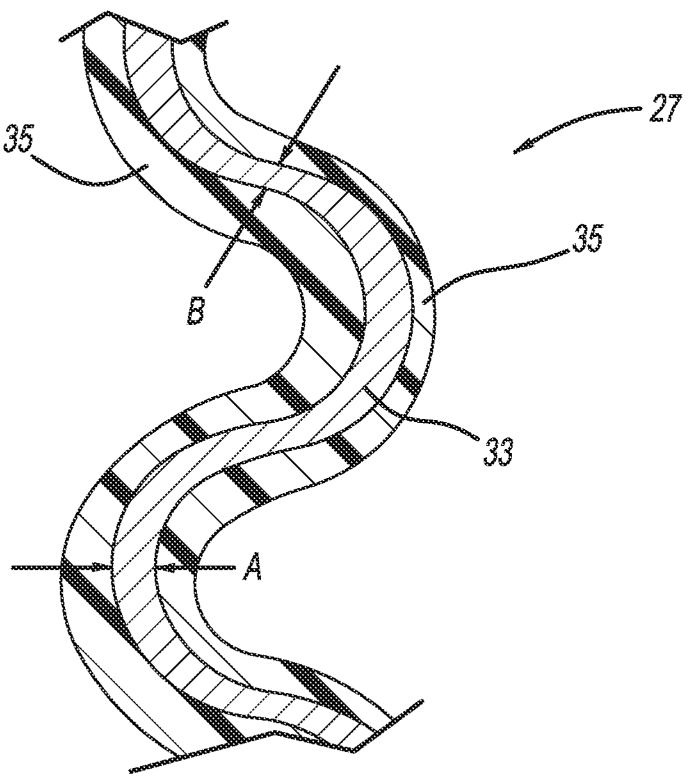
FIG - 5

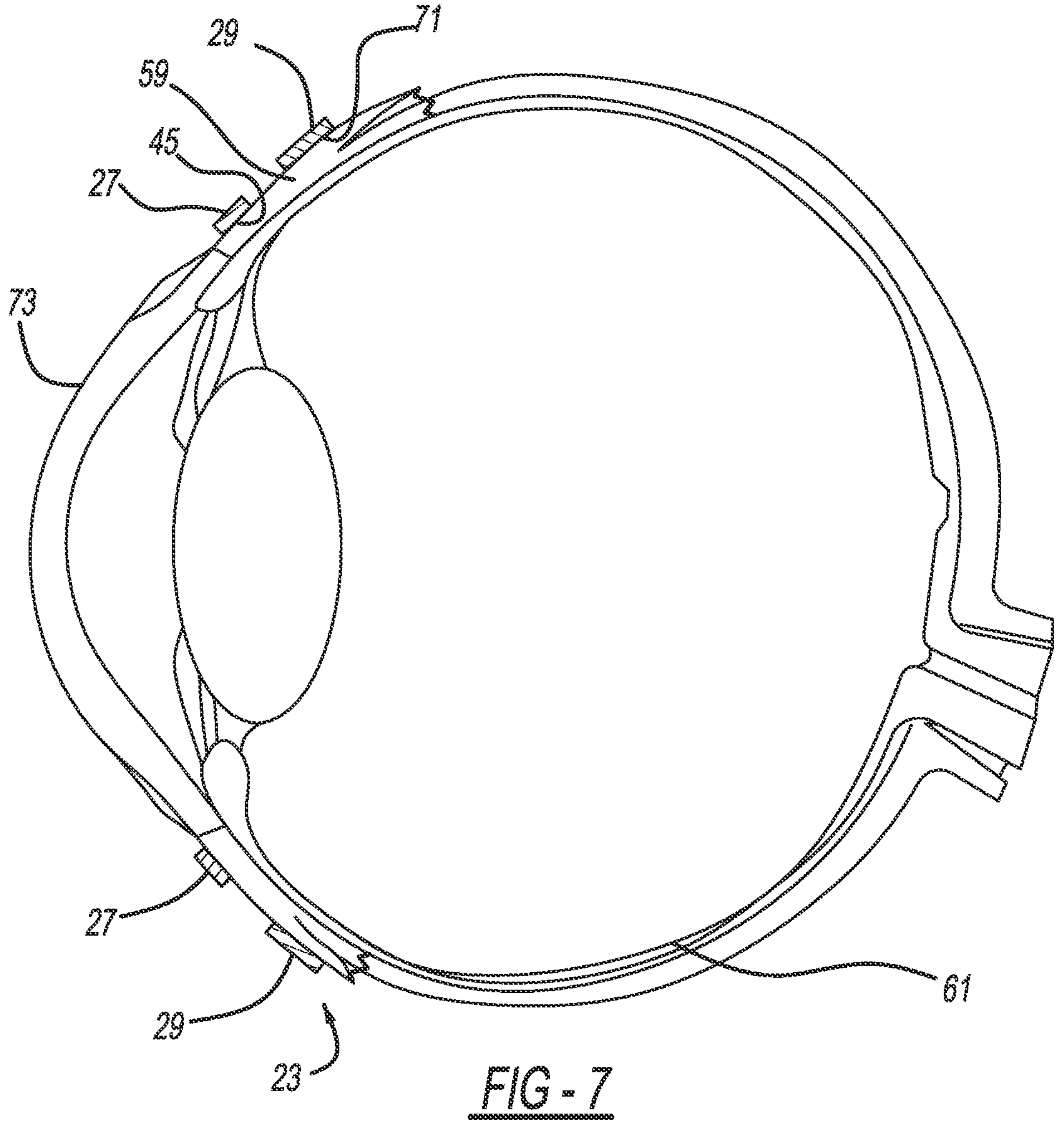
FIG - 7
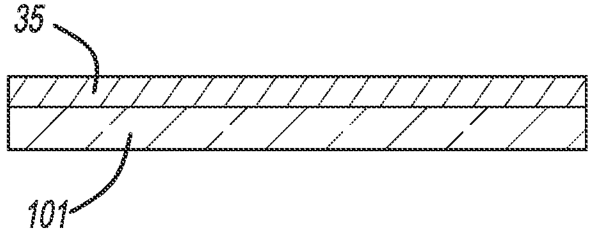
FIG - 9A
FIG - 9B
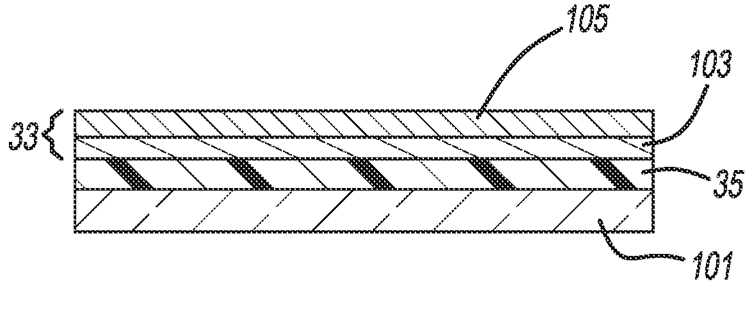

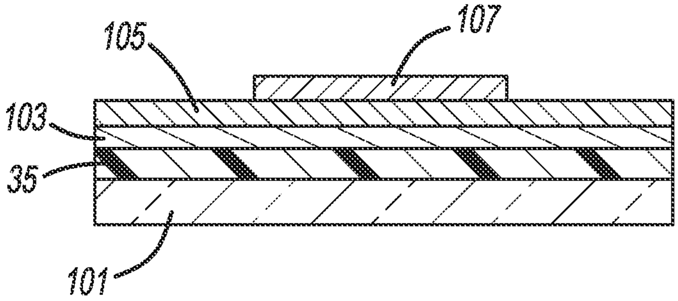
FIG - 9C
FIG - 9D
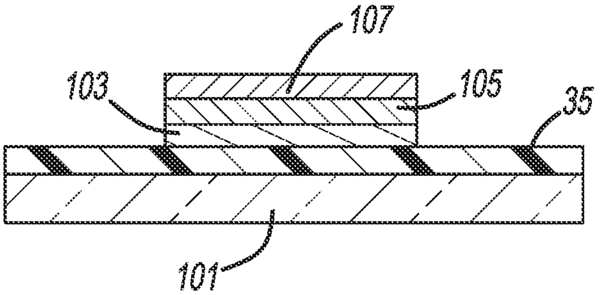
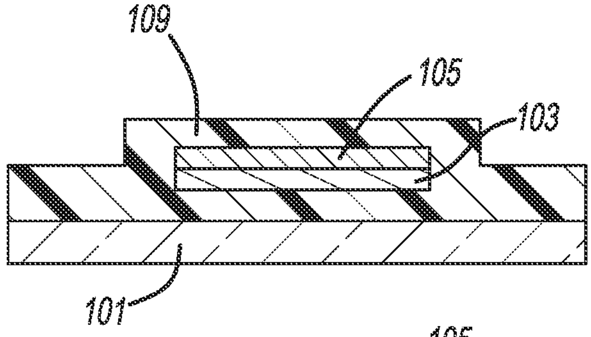
FIG - 9E
FIG - 9F
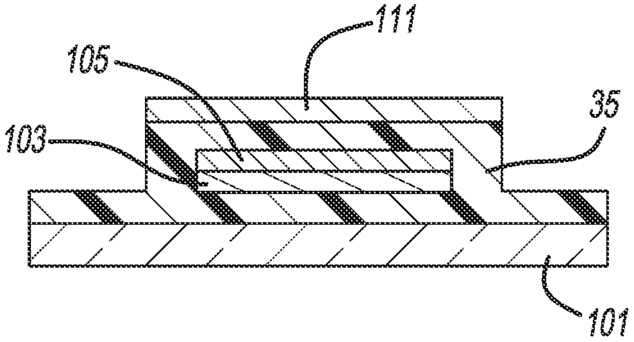
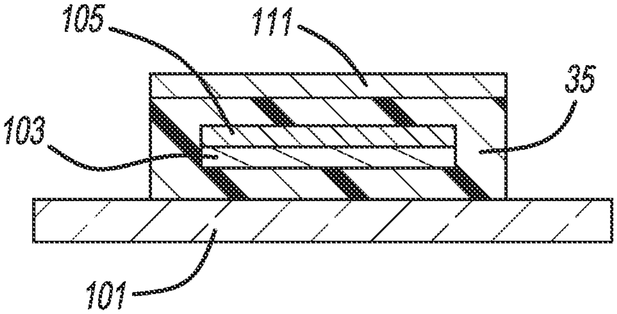
FIG - 9G
FIG - 9H
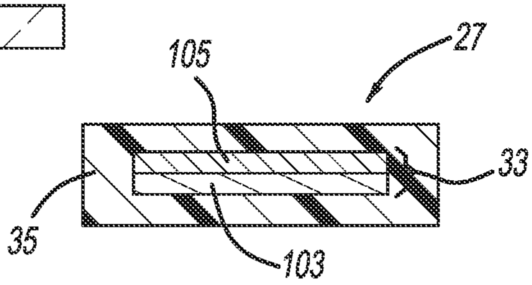

INTRAOCULAR PRESSURE SENSOR

CROSS-REFERENCE TO RELATED APPLICATIONS

This application is a divisional of U.S. patent application Ser. No. 16/494,894 filed on Sep. 17, 2019, which is a national phase entry of PCT international Patent Application No. PCT/US2018/023502 filed on Mar. 21, 2018, which claims the benefit of U.S. Provisional Application No. 62/474,750 filed on Mar. 22, 2017, which are all incorporated by reference herein.

BACKGROUND AND SUMMARY

The present disclosure relates generally to pressure sensors and more particularly to a wireless intraocular pressure sensor system including a deformable inductor.

Glaucoma is the second leading cause of blindness which is an asymptomatic, progressive and irreversible disease that is usually associated with elevated intraocular pressure. Most conventional constructions of intraocular pressure sensors can be categorized into three general groups in terms of their energy transferring mechanisms: active, passive, and radio-frequency-powered devices.

Active devices traditionally employ application specific integrated circuits that can store, process and transmit data. However, they make the overall device large, heavy and inflexible. Furthermore, such active systems typically require an integrated battery or power-receiving coil, which both add to the weight and size of the device.

Traditional passive sensors require high precision surgery to anchor the device to the iris. The fabrication process for such passive devices is typically complex and expensive. Furthermore, such traditional passive sensors require an external reading mechanism of an undesirably large size that interferes with the vision of the patient thereby making it unsuitable for wearable long term measurements.

Conventional radio frequency or electromagnetic coupled sensors have employed variable capacitors to sense pressure. These variable capacitors, however, require a pressurized reference chamber that has great difficulty in sustaining its baseline pressure over time due to packaging imperfections. This causes significant undesirable signal drift due to the leakage.

Exemplary prior intraocular pressure sensors are disclosed in U.S. Pat. No. 9,289,123 entitled “Contact Lens for Measuring Intraocular Pressure” which issued to Weibel et al. on Mar. 22, 2016, and U.S. Patent Publication No. 2016/0051144 entitled “Systems and Methods for Monitoring Eye Health” which published to Rickard et al. on Feb. 25, 2016. Both of these are incorporated by reference herein. It is noteworthy that Weibel includes a considerable quantity of electronic components. Moreover, Rickard uses only capacitive sensing and requires surgical implantation into the eye.

In accordance with the present invention, a pressure sensor system is provided. In another aspect, a wireless intraocular pressure sensor includes a deformable or stretchable inductor. A further aspect of an intraocular pressure sensing system includes a deformable and variable inductor, within a ring-shaped carrier layer, sized to contact an eye. Another aspect provides an organ pressure sensing system including a passive inductor with a wavy, undulating or serpentine shape. In yet another aspect, a biomedical pressure sensor includes a deformable inductor having an undulating pattern along at least a majority of its length, a deformable outer ring spaced away from and surrounding the inductor, and elongated connectors or arms spanning between the inductor and an outer ring, with the connectors being radially elongated and causing deformation of an adjacent portion of the inductor when the outer ring is deformed or moved due to internal body pressure. A method of making and/or using a wireless intraocular pressure sensor, including a deformable inductor, is also provided.

The present pressure sensor is advantageous over conventional devices. For example, the present pressure sensor functions as a passive strain gauge that synergistically serves as both a pressure sensitive element and a wireless communications interface. It advantageously does not obstruct the vision of the patient, as compared to conventional cornea-mounted devices. Furthermore, in one exemplary construction, the present system is intended to be a temporarily worn device that is easily removable or dissolvable after a predetermined period of time, and does not require surgical in vivo implantation or removal. Another exemplary construction in vivo implants only a passive sensor for use with a portable or temporarily adhered reader. Moreover, the present system advantageously includes only minimal electronic components, such as a single capacitor, located in the sensor device inserted onto the eye; this provides a much lighter weight and lower cost device which does not obstruct the patient’s vision. Additional advantages and features of the present system and method will become apparent from the following description and appended claims, taken in conjunction with the associated drawings.

BRIEF DESCRIPTION OF THE DRAWINGS

FIG. 3 is a cross-sectional view, taken along line 3-3 of FIG. 2, showing the first embodiment present intraocular pressure sensor;

FIG. 4 is a cross-sectional view, taken along line 4-4 of FIG. 2, showing the first embodiment present intraocular pressure sensor;

FIG. 5 is a longitudinal sectional view, taken along line 5-5 of FIG. 3, showing the first embodiment present intraocular pressure sensor;

FIG. 7 is a cross-sectional view showing the first embodiment present intraocular pressure sensor on an eye;

FIG. 9A-H are a series of cross-sectional views showing a manufacturing process for the present intraocular pressure sensor for all embodiments;

DETAILED DESCRIPTION

Figure 1:
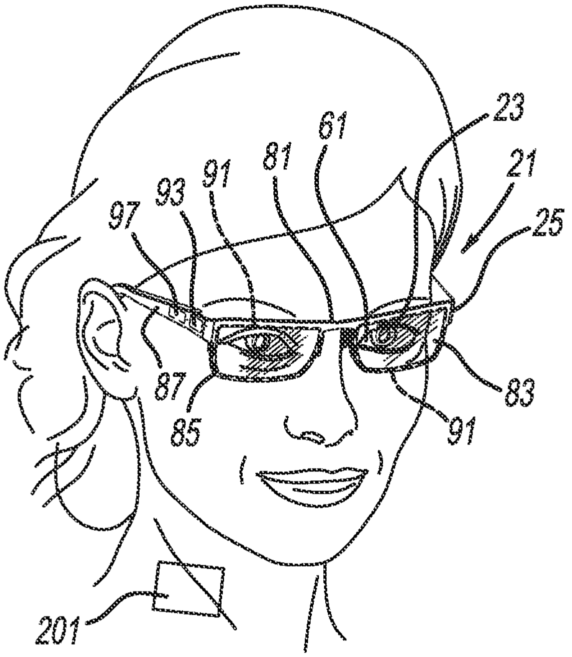
FIG. 1 is a perspective view showing a first embodiment of the present intraocular pressure sensor system as worn on a patient.

A first embodiment of an intraocular pressure sensing system 21 is shown in FIGS. 1-8, and includes an intraocular pressure sensor 23 and a reader 25. Sensor 23 includes a sensing and transmitting coil assembly 27, an outer ring 29 and a plurality of connecting arms 31 spanning between the spaced apart coil assembly 27 and outer ring 29. Coil assembly 27 has a looped metallic inductor 33 at least partially encapsulated within a protective polymeric layer or casing 35. Inductor 33 is preferably made from layers of titanium and copper, titanium and gold, or an alloy thereof. Alternately, other metallic or conductive polymeric materials may be employed although they may not be as advantageous.

Inductor 33 and protective layer 35 have an undulating, serpentine or wave-like shape along a curved length thereof, defined by alternating peaks and valleys with curved diagonal walls connecting therebetween. As will be described in greater detail hereinafter, the undulating shape allows inductor 33 to be deformed and stretchably expanded at any point therealong. FIG. 5 illustrates an increased width A of the inductor at each peak and valley which is greater than width B at each of the diagonal connecting walls. This effectively adds increased material at the peak and valley areas which are more prone to fracture when expanded or deformed. However, an eye-facing inner surface 41 and an opposite outer surface 43 of inductor 33 are preferably substantially flat. Furthermore, the corresponding eye-facing inner surface 45 and opposite outer surface 47 of protective layer 35 are preferably substantially flat, but for optionally curved corners.

At least three and more preferably at least four connecting arms 31 are spaced away from each other with open gaps 51 therebetween. Each connecting arm 31 is radially elongated away from a center point of sensor 23. Moreover, each connecting arm 31 is integrally and directly connected to an outer periphery of protective layer 35 of sensor 27 and to an inside diameter surface 53 of outer ring 29. Each connecting arm 33 is preferably at least five times as long as wide C and at least twice as wide C as thick D. This dimensional arrangement allows connecting arms 31 to have a partially spherical or curved side view shape between their opposite ends to match the eye's shape. This dimensional configuration also allows for torsional flexure with minimal linear or radial stretch of the connecting arms. Notwithstanding, these exemplary dimensions may be varied.

Outer ring 29 preferably has a circular or arcuate outer periphery 55. A width E of outer ring 29 is preferably at least five times width C of each connecting arm 31 and at least ten times that of coil assembly 27. Notwithstanding, these exemplary dimensions may be varied. Outer ring 29 and coil assembly 27 are coaxial with gaps 51 therebetween. Multiple apertures 57 are disposed through the thickness of outer ring 29 for mechanically receiving and interlocking with a biocompatible adhesive applied to temporarily hold outer ring 29 to a sclera 59 of eye 61. The polymeric material for outer ring 29, connecting arms 39 and protective layer 35 is preferably Parylene-C (obtained from Parylene Coater-Specialty Coating System as PDS 2010), Sylgard® 184 Silicone Elastomer (obtained from Dow Corning), Polymethyl Methacrylate (obtained from MicroChem Corporation)) or the like.

A single electrical component, preferably a capacitor 63, is electrically connected to ends of inductor 33 and secured to sensing coil assembly 27. This is preferably the only electronic component directly attached to sensor 23, such that a battery, microprocessor and other solid state electrical components are not required, thereby saving weight and reducing cost.

Figure 2:
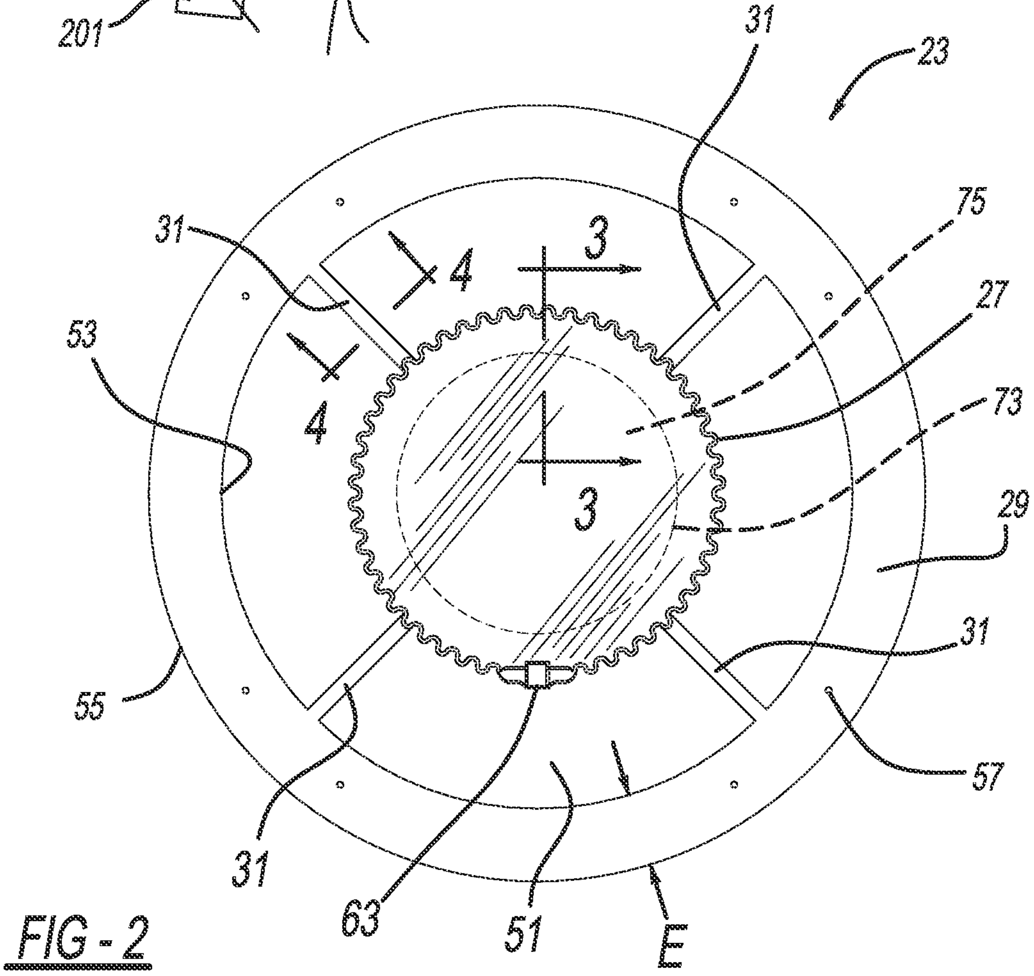
FIG. 2 is a front elevational view showing the first embodiment of an intraocular pressure sensor of the present system.

The placement of sensor 23 relative to an organ, specifically a patient's eye 61, can best be observed in FIGS. 2 and 7. An inner surface 71 of outer ring 29 is temporarily mounted to sclera 59 by a dissolvable adhesive such as a hydrogel based adhesive. Inner surface 71 may optionally have a partial dome shape to conform to the sclera. Connecting arms 31 and sensing coil assembly 27, however, are free of an adhesive and allowed to move relative to eye 61. Sensing coil assembly 27, connecting arms 31 and outer ring 29 are all external to and outside of a periphery of a cornea 73 of eye 61. Nevertheless, an optional dissolvable polymeric film 75, of a generally dome-like shape, spans between an inside edge of sensor coil assembly 27 and initially spans across cornea 73. This optional central film 75 is simply intended to add temporary supporting structure to the thin and deformable sensing coil assembly 27 during user or doctor insertion onto the eye and is intended to dissolve away within a day or two thereafter such that there is an unobstructed central opening over the cornea during normal sensing use. Outer ring 29, connecting arms 31, protective layer 35 and optional central film 75 are all substantially transparent.

Figure 6:
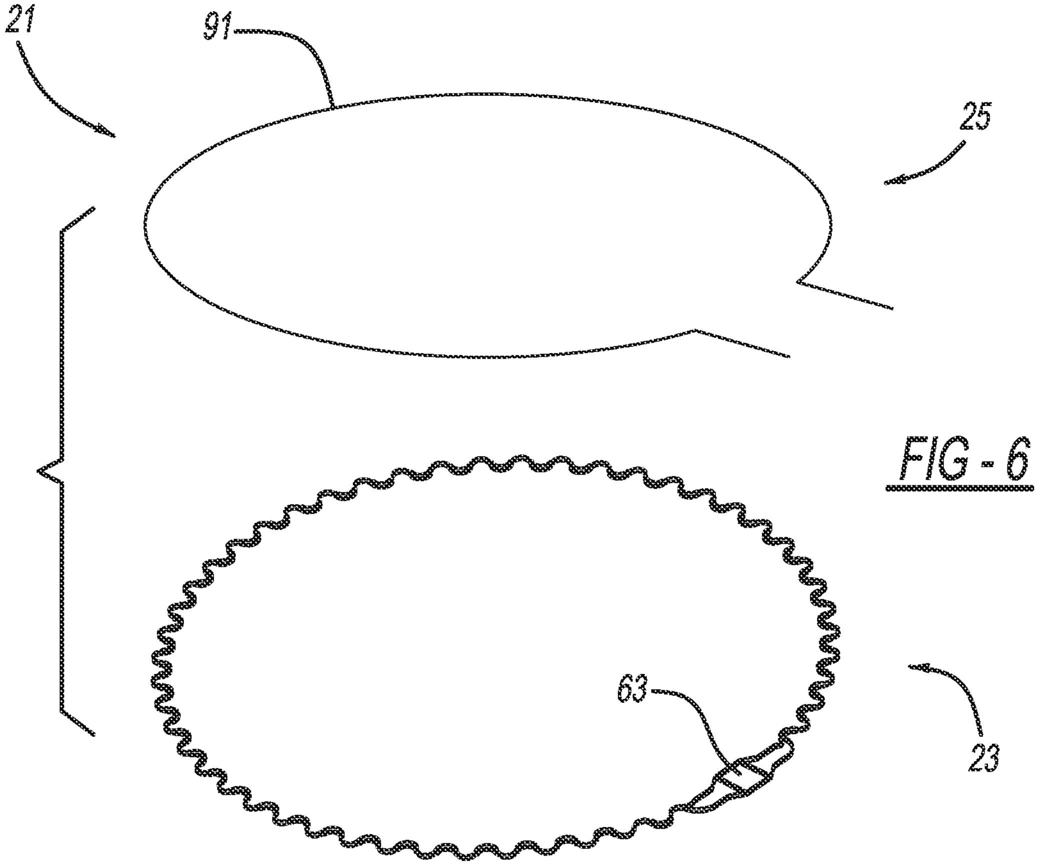
FIG. 6 is a diagrammatic and exploded perspective view showing the first embodiment present intraocular pressure sensor system.
Figure 8:
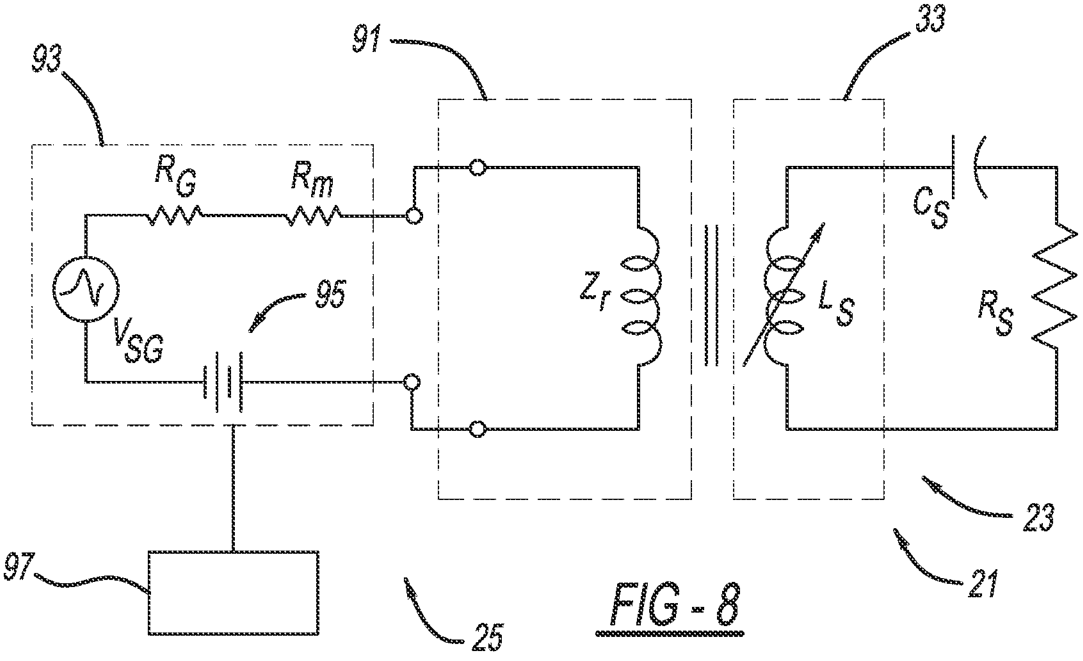
FIG. 8 is a circuit diagram of the first embodiment present intraocular pressure sensor system.

Referring now to FIGS. 1, 6 and 8, reader 25 is preferably mounted to eyeglasses 81 which include transparent lenses 83, a frame 85 and earpieces 87. A reading coil or wire 91 is encapsulated within or adhered to an inside surface of eyeglass frame 85 generally surrounding each lens 83. Ends of the looped reading coil 91 are electrically connected to an electrical circuit 93 including a battery 95 for a wearable/portable reader or other power supply accessed through a wall outlet plug for a stationary reader, a signal generator voltage source ($V_{SG}$), a signal generator internal resistor ($R_G$), and a measurement resistor ($R_M$). In the circuit diagram, reading coil 91 is shown as a receiver coil impedance inductor ($Z_r$). Further in the circuit diagram of FIG. 8, constant capacitor 63 is shown as $C_S$, a parasitic resistor function of the inductor is shown as $R_S$, and variable inductor 33 is illustrated as $L_S$.

Periodic electromagnetic transmissions are sent from the reader coil to the passive sensor coil to activate a resonant frequency of the sensor coil. This resonant frequency is based on the geometries of the inductor and capacitor, and has an exemplary frequency of 100 MHz to 1 GHz, which can be varied depending on the detectable frequency range of the impedance analyzer. Readout signals of the reader coil are impedance amplitude and phase over this frequency range to characterize the resonant frequency, where a phase dip is observed if the inductor is deformed. The phase dip is an indicator of the resonant frequency such that when the sensing inductor is deformed in response to pressure variation, a frequency shift of this phase dip can be detected.

Referring now to FIGS. 2 and 6-8, if intraocular pressure outwardly bulges or expands sclera 59 of eye 61 then outer ring 29 of sensor 23 will move off its nominal inner surface 71 position and/or radially move from its nominal circular position. This will move at least one of the adjacent connecting arms 31 in a linear and/or torsional manner. This movement of connecting arm 31 will subsequently deform, flex or circumferentially expand inductor 33 away from its nominal free position which will accordingly change an inductance value received by reader coil 91 from inductor 33. The sensor serves as a planar and circular LC passive resonator that has a constant capacitor and a stretchable variable inductor. The self-inductance of the inductor, the parasitic capacitance between the segments, and the Q-factor are all changeable by the expansion of the sensor diameter. In addition, the mutual inductance between the sensing coil and reader coil will also change as the sensing coil deforms. This phenomenon is employed to measure the strain and the eye tissues induced by intraocular pressure elevation. Accordingly, the change of self-inductance in parasitic capacitance results in the change of resonance frequency of the LC loop. Therefore, the pressure variance can be read by the impedance analyzer through a frequency drift. The resultant output from impedance analyzer 93 of reader 25 is transmitted via communications transmitter 97 to a handheld or stationary computer device, through a Bluetooth standard, a Wi-Fi standard, an RFID standard, a ZigBee standard or the like. This sensor deformation provides an advantageous method of use.

A preferred manufacturing or fabrication process for at least the sensing coil assembly 27 portion of sensor 23 is illustrated in FIGS. 9A-H. Two masks are employed. As shown in FIG. 9A, polymer 35 is deposited in a chemical vapor deposition process. First, a glass wafer or substrate 101 is coated with five μm of Parylene-C polymer 35, a twenty nm layer of titanium and a 700 nm layer of copper, 103 and 105 respectively, which will become inductor 33. This is shown in FIG. 9B. Second, metallic layers 103 and 105 are evaporated using a thermal evaporator. A photoresist layer 107 or first mask is used to pattern the undulating shape using ultraviolet photolithography and thereafter wet-etching as illustrated in FIGS. 9C and 9D. Third, photoresist layer 107 is subsequently added on top of the copper layer 105. Fourth, surface mounted capacitor 63 (see FIG. 2) is soldered to the end contacts of inductor 33 using silver epoxy. Fifth, FIG. 9E illustrates applying another five μm polymeric coating at 109 to fully encapsulate the inductor layers. Sixth, FIG. 9F shows a layer of aluminum 111 deposited on top of outermost polymeric layer 109 and patterned using a second photoresist layer mask to form an aluminum mask that protects the sealed metallic inductor core during subsequent plasma dry etching of the polymeric casing to create the trimmed form shown in FIG. 9G. Finally, FIG. 9H shows the completed sensing coil assembly 27 separated from the glass substrate and with the aluminum mask removed. The connecting arms and outer ring are also simultaneously formed in an integral and one piece manner with the polymeric encapsulating layers.

The completed inductor preferably has a thickness F (see FIG. 3) of approximately 500-900 nm and more preferably 720 nm. A thickness G of protective polymeric layer 35 on each inner and outer surface is approximately 3-10 μm and more preferably 4-5 μm. Alternately, the inductor and/or polymeric layers can be two-dimensionally or three-dimensionally printed. Furthermore, the polymeric material may alternately be coated onto the metallic inductor by spinning, chemical vapor deposition, dipping at room temperature, or spraying. Moreover, the inductor may alternately be produced by using 2-D printing, e-beam evaporations, vapor deposition, sputtering, electroplating or electroless plating.

Figure 10:
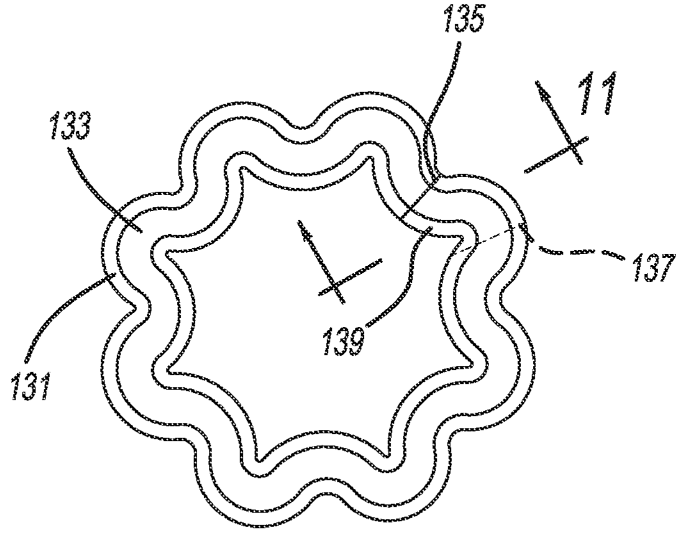
FIG. 10 is a front elevational view showing an alternate embodiment of the present intraocular pressure sensor.
Figure 11:
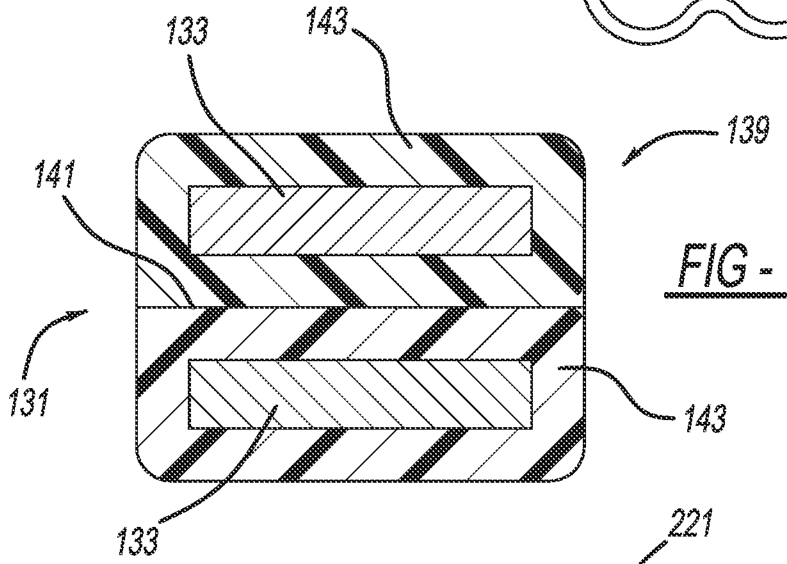
FIG. 11 is a cross-sectional view, taken along line 11-11 of FIG. 10, showing the alternate embodiment intraocular pressure sensor.

Reference should now be made to FIGS. 10 and 11 for an alternate embodiment of the present pressure sensor. In this construction, a generally annular sensing coil assembly 131 includes an undulating inductor coil 133 at least partially encapsulated in a protective polymeric casing or layer 143. Connecting arms and an outer ring such as in the prior embodiment are also included although not presently shown. Ends 135 and 137 of sensing coil assembly 131 extend past each other such that distal segments 139 overlap each other in a stacked manner with an adhesive therebetween to secure together internal facing surfaces 141 thereof.

If an adhesive is not employed in a variation thereof, the integrated sensing inductor and capacitor can be microfabricated using a metal-polymer sandwich. Such can be manufactured by: first, depositing a polymeric bottom layer; second, depositing and patterning a bottom metal plate layer of the capacitor; third, deposition and patterning of a polymeric dielectric layer on top of the metal plate; fourth, depositing and patterning a top metal plate layer; then fifth, encapsulating the top capacitor plate within a polymeric material.

Polymeric layer 143 encapsulating inductor 133 serves as a predominantly non-conductive insulator between the overlapped ends of inductor 133 at overlapping segment 139. Thus, overlapping segment 139 functions as a capacitor integrated as a synergistic and multifunctional construction along with the sensing inductance and signal transmitting antenna-like functions. The microfabricated version advantageously eliminates the capacitor assembly steps and improves device reliability and production yield. Accordingly, a separate capacitor component is not required. It should be appreciated that while it is preferred to use this integrated inductor and capacitor device for a wireless intraocular pressure sensor, it should also be appreciated that this device may alternately be applied to a variety of other types of biomedical sensors that are attached to or implanted in a patient.

Figure 12:
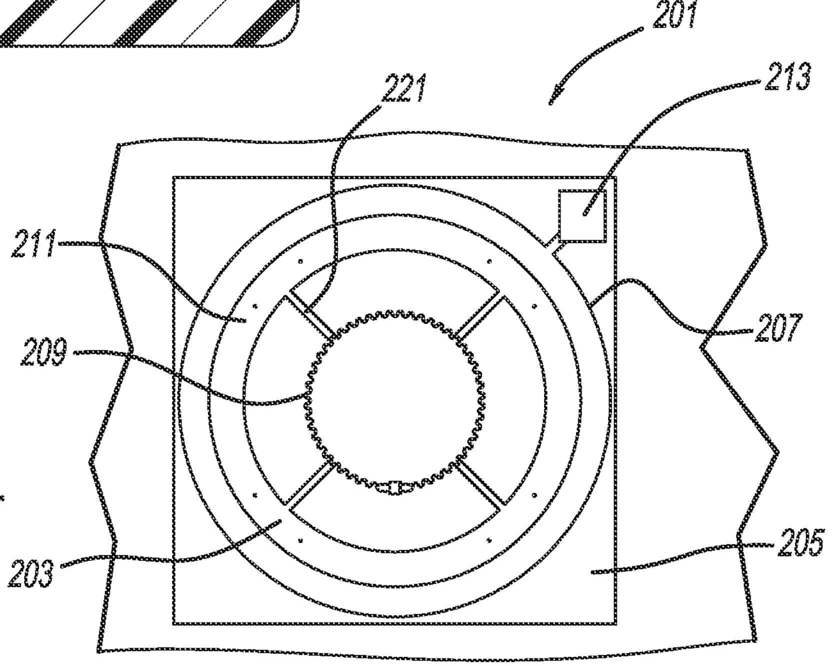
FIG. 12 is a front-elevational view showing another alternate embodiment intraocular pressure sensor system.

FIG. 12 illustrates yet another alternate embodiment biomedical pressure sensor 201. In this exemplary configuration, sensor system 201 includes a passive sensor 203 essentially the same as with the first embodiment of FIG. 2, however, it is mounted to an internal patient-side or encapsulated within a patch 205. Patch 205 is preferably a flexible film or sheet of polymeric material with a pressure sensitive adhesive on the internal side thereof. Furthermore, a looped reading coil wire 207 is attached to one of the surfaces of patch 205 or encapsulated therein. Reading coil wire 207 coaxially surrounds inductor 209 and an outer ring 211 without directly contacting inductor 209. Impedance analyzer and communications circuitry 213 and associated electronics are electrically connected to reading coil wire 207 and mounted to an outside surface of patch 205. As shown in FIG. 1, sensor system 201 is removably adhered to external skin area of the patient so as so sense blood pressure, heart rate, or other patient-induced movements which deform the outer ring, connecting arms 221 and the inductor.

An alternate design employs a wearable sensing watch with the impedance analyzing circuitry and a digital display constructed on an outside surface of a patch, which is electrically connected to a reading coil wire. The watch is wrist mounted by a strap, and includes a timekeeping clock circuit in addition to the reading circuit, but is otherwise like that shown in FIG. 12. In this construction, there is no need for communications circuitry to transfer data to a separate reader.

Figure 13:
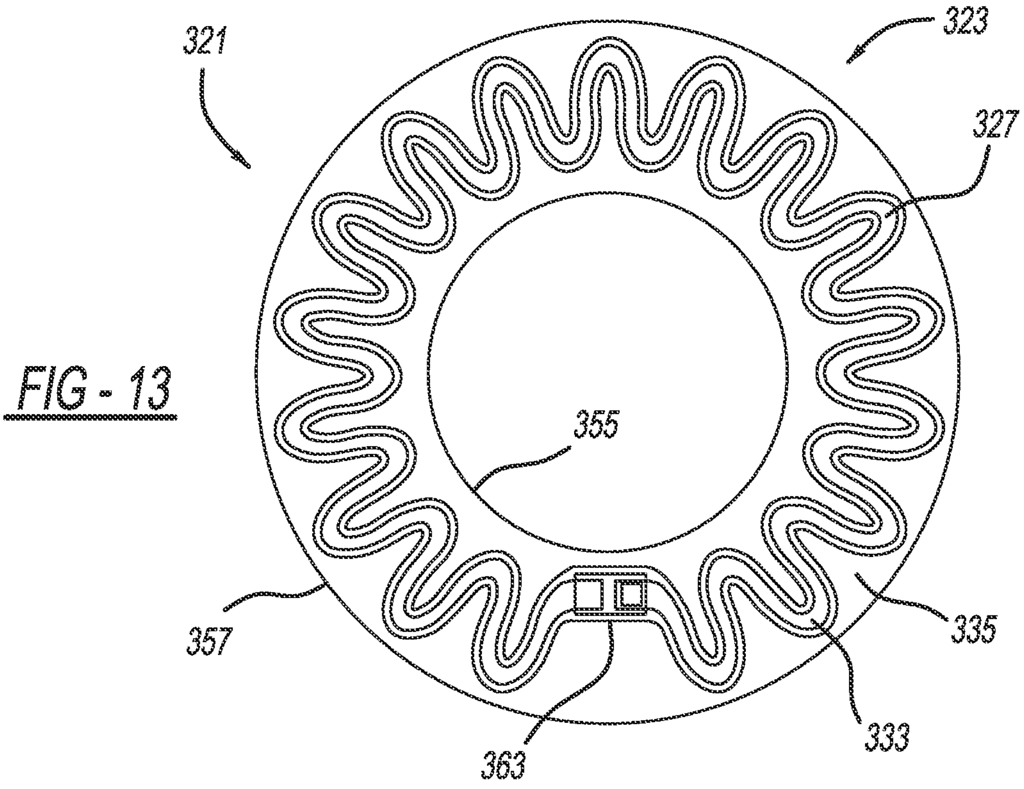
FIG. 13 is a front elevational view showing a second embodiment of an intraocular pressure sensor of the present system.
Figure 14:
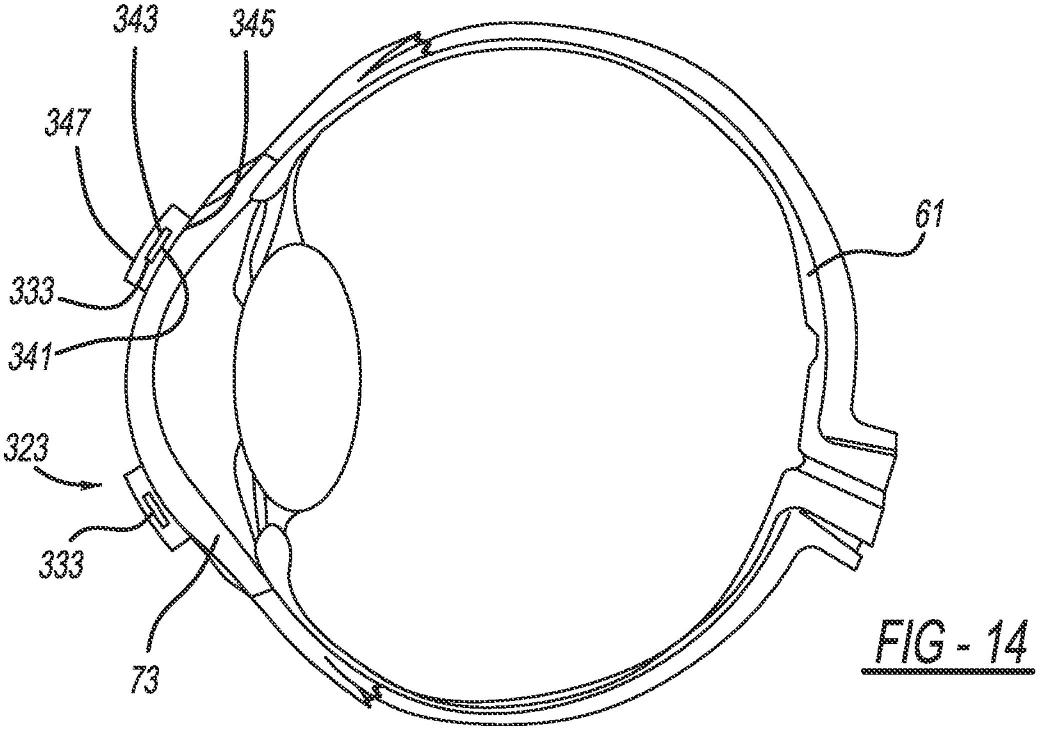
FIG. 14 is a cross-sectional view showing the second embodiment present intraocular pressure sensor on an eye.

A second major embodiment of an intraocular pressure sensing system 321 is shown in FIGS. 13 and 14, and includes an intraocular pressure sensor 323 used with the previously disclosed reader 25 (see FIG. 1). Reader 25, however, includes an analog front-end circuit for impedance measurements and a user friendly control panel or display, in addition to a conductive coil, a microprocessor controller and a power supply like a battery.

Sensor 323 includes a sensing and transmitting coil assembly 327 embedded in a donut shaped or ring-like carrier or protective layer 335. Protective layer 335 has concentric inner and outer edges 355 and 357, respectively. Coil assembly 327 has a looped metallic inductor 333 at least partially encapsulated within protective and insulating layer 335 which is polymeric. Inductor 333 is a variable inductor.

Inductor 333 has an undulating, serpentine or wave-like shape along a curved length thereof, defined by alternating peaks and valleys with curved diagonal walls connecting therebetween. The undulating shape allows inductor 333 to be deformed and stretchably expanded at any point therealong. The materials and manufacturing process for this exemplary inductor and protective layer can optionally be the same as for the first embodiment. Alternately, coil assembly 327 is optionally placed into a mold designed for the size and curvature of the cornea to which it will be applied. The mold is thereafter filled with a polymer (e.g., PDMA, PDMS or HEMA) and the material is polymerized by heating or exposure to UV light to create the desired final shape for carrier layer 335.

An eye-facing inner surface 341 and an opposite outer surface 341 of inductor 333 are preferably substantially parallel to each other and flat. Furthermore, the corresponding eye-facing inner surface 345 and opposite outer surface 347 of protective layer 335 are preferably substantially parallel to each other, and may optionally include curved corners and curved intersecting sides. Eye-facing inner surface 345 of protective layer 335 contacts against and is positioned over cornea 73 of eye 61 adjacent a periphery thereof. If intraocular pressure outwardly expands and stretches the cornea, this stretching will subsequently deform, flex or circumferentially expand inductor 333 away from its nominal free position which will accordingly change an inductance value received by the reader coil from inductor 333.

The electrical circuit function of the second embodiment organ sensing system 321 is similar to that shown in FIG. 8. The present use of a variable inductor in an LCR tank, parallel resonance circuit for strain sensing is incorporated for intraocular organ pressure sensing. It employs a flexible and stretchable conductive element which is achieved using serpentine geometry. The capacitance in series with the inductor is achieved on-chip and is a constant capacitor in the range of 5 picoFarads (for both the capacitor 363 in FIGS. 13 and 63 in FIG. 2). The inductor diameter is near 11 millimeters that results in a variable inductor near 35 nano Henries. The parasitic resistance is below 10 ohms that results in a good quality factor. Furthermore, the mean resonance frequency of the LCR tank is near 500 Megahertz. It should be appreciated, however, that these specific exemplary values will be optimized for different organ applications, and therefore, may vary. The stretchable inductor is placed around the corneoscleral joint and the sensor stretches and changes the inductor's diameter when elevation of intraocular pressure changes the circumferential curvature of the cornea. The curvature change is transferred to the stretchable inductor partially through the carrier layer that holds and packages the inductor inside, without the need for supplemental hermetic packaging of electronics.

Figure 15:
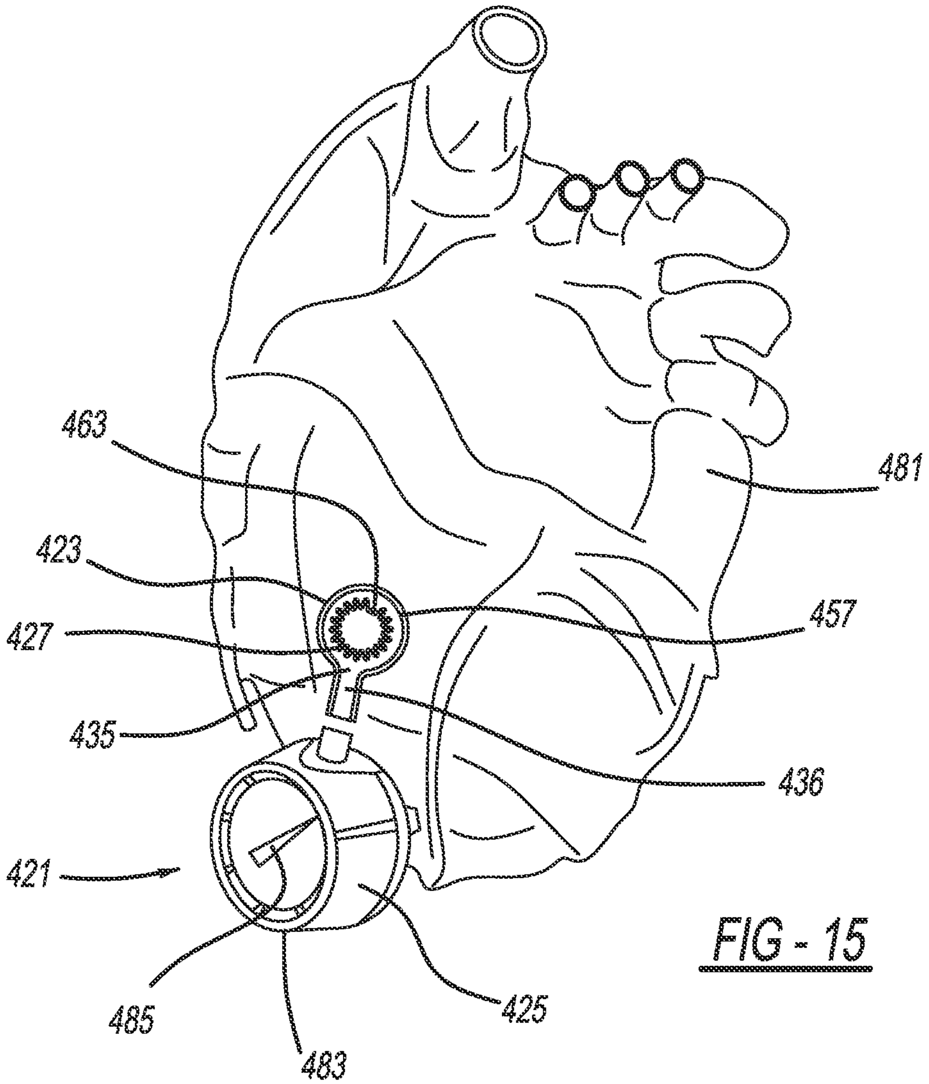
FIG. 15 is a perspective view showing a third embodiment of a cardiovascular pressure sensor system.

Another alternate embodiment is illustrated in FIG. 15. This construction employs a pressure sensing system 421 including an in vivo organ pressure sensor 423 and an ex vivo reader 425. Sensor 423 has a sensing and transmitting coil assembly 427 embedded and encapsulated in an insulating polymeric protective carrier or layer 435. This layer 435 may have an inner edge defining a central opening or may be solid, continuously spanning across the central area as is illustrated. An elongated tail 436 may optionally extend from a peripheral and generally circular and arcuate outer edge 457 of layer 435.

Coil assembly 427 includes a looped or serpentine wavy metallic inductor, and a capacitor electronic component 463 attached thereto. Sensor 423 is passive, without a microprocessor or battery attached thereto. Layer 435 is adhesively bonded to an outside surface of a cardiovascular organ 481, such as a heart or blood vessel, by a bioadhesive or less preferably, sutured thereto.

Reader 425 is a handheld and portable impedance analysis unit or module (as illustrated) within a housing 483 containing a battery power supply, microprocessor, reading coil and electrical circuit, as with the first embodiment. An analog output display dial 485 or digital display screen with numeric values may also be employed. Reader is removably placed against the patient's skin to activate sensor 423 remotely located therefrom, and to obtain a pressure measurement therefrom. Alternately, a removable adhesively bonded reader, like that shown as 201 in FIG. 1, may be employed with in vivo sensor 423.

Reader 425 employs a secondary inductor integrated to an impedance analysis circuitry, where the phase of the readout coil shows a 'dip' nearby the resonant frequency of the sensor. Impedance measurements can use various methods such as a bridge method, resonant method, I-V method, RF I-V method, network analysis method and auto balancing bridge method. Preferably, an I-V method is employed for the reader electrical circuit. This method provides high accuracy and a wide impedance range at higher frequencies like 500 MHz. It applies an electrical current to a reference impedance in series with the readout coil and measures the voltage across the readout coil within a specific frequency range that covers the resonant frequency of the sensor. The coupling coefficient between the sensor and the readout coil is reflected to the readout impedance and measured by the module.

While various embodiments of the present sensor system have been disclosed, it should be appreciated that other variations may be made. For example, alternate electrical circuits and electronic components may be used although some of the present benefits may not be realized. Furthermore, different materials and manufacturing process steps can be used, however, certain of the present benefits may not be achieved. For example, the sensing coil assembly and protective layer may be entirely made from biodissolvable material such that the sensor does not need to be manually removed from the eye. The features of any of the embodiments may be mixed and matched in an interchangeable manner with any of the other embodiments disclosed herein. Various changes and modifications are not to be regarded as a departure from the spirit or the scope of the present invention.

The invention claimed is:

1. A method of making a pressure sensor, the method comprising:

(a) depositing a polymeric bottom layer;

(b) depositing a first metallic layer on the polymeric bottom layer;

(c) depositing a middle polymeric layer on the first metallic layer;

(d) depositing a second metallic layer on the intermediate polymeric layer such that the first and second metallic layers overlap with the middle polymeric layer therebetween;

(e) depositing a polymeric upper layer on the upper metallic layer;

(f) the polymeric layers encapsulating a majority of the metallic layers therein;

(g) creating an undulating shape to at least one of the metallic layers which is an inductor, the undulating shaped inductor being stretchably expandable to operably change a readout signal of the pressure sensor; and (d) the metallic layers being configured to sense inductance and transmit a signal outside of the sensor, with the overlapping metallic layers being a capacitor.

2. The method of claim 1, further comprising creating a wireless, intraocular pressure sensor from the layers, the undulating shaped inductor being configured to surround and be external to a cornea of an eye without in vivo implantation and without obstructing vision of the eye.

3. The method of claim 2, further comprising creating a central opening in the layers with polymeric material located between the metallic layers and the central opening of the sensor, and with polymeric material located between the metallic layers and a peripheral edge of the sensor.

4. The method of claim 3, wherein a multifunctional inductor and antenna is a single loop of the metallic layers with the overlapping first and second metallic layers creating end segments of the single loop.

5. The method of claim 2, further comprising sensing intraocular pressure and transmitting an output from the undulating shaped which is a single looped flexible inductor, of the metallic layers, to a remote reader, without a microprocessor or battery mounted to the sensor.

6. The method of claim 1, wherein the depositing of the metallic layers includes printing metallic material.

7. The method of claim 1, wherein the depositing of the metallic layers includes at least one of: vapor depositing, sputtering, electroplating, or electroless plating.

8. The method of claim 1, wherein the depositing of at least one of the metallic layers includes patterning the undulating shape using photolithography and then wet-etching.

9. The method of claim 1, further comprising creating the pressure sensor to be 500-900 nm for one of the metallic layers, 3-10 μm for the polymeric bottom layer, and 3-10 μm for the polymeric upper layer.

10. A method of making a pressure sensor, the method comprising:

(a) depositing a polymeric bottom layer;

(b) depositing a first metallic layer on the polymeric bottom layer;

(c) depositing a middle polymeric layer on the first metallic layer;

(d) depositing a second metallic layer on the intermediate polymeric layer such that the first and second metallic layers overlap with the middle polymeric layer therebetween;

(e) depositing a polymeric upper layer on the upper metallic layer;

(f) creating an undulating shape to at least one of the metallic layers;

(g) causing the pressure sensor to be configured to sense inductance due to intraocular pressure and transmit a wireless signal outside of the sensor; and (h) the at least one of the metallic layers with the undulating shape being configured to surround and be external to a cornea of an eye without in vivo implantation and without obstructing vision of the eye.

11. The method of claim 10, wherein:

the polymeric layers encapsulate a majority of the metallic layers therein;

the overlapping metallic layers are configured to act as a capacitor;

the pressure sensor is without a microprocessor or battery thereon; and the at least one of the metallic layers with the undulating shape being an expandable inductor after the encapsulation thereof.

12. A method of making a pressure sensor, the method comprising:

(a) depositing a polymeric bottom layer;

(b) depositing a first metallic layer on the polymeric bottom layer;

(c) depositing a middle polymeric layer on the first metallic layer;

(d) depositing a second metallic layer on the intermediate polymeric layer such that the first and second metallic layers overlap with the middle polymeric layer therebetween;

(e) depositing a polymeric upper layer on the upper metallic layer;

(f) creating an undulating shape to at least one of the metallic layers;

(g) creating a circular peripheral edge of the polymeric layers, and inwardly spacing peaks and valleys of the undulating shaped of the metallic layers away from the peripheral edge;

(h) creating a multifunctional inductor and antenna from a single loop of the metallic layers, with the overlapping first and second metallic layers creating end segments of the single loop; and (i) causing the pressure sensor to be configured to sense inductance due to intraocular pressure and transmit a wireless signal outside of the sensor.

13. The method of claim 10, wherein the depositing of the metallic layers includes printing metallic material.

14. The method of claim 10, wherein the depositing of the metallic layers includes at least one of: vapor depositing, sputtering, electroplating, or electroless plating.

15. The method of claim 10, wherein the depositing of at least one of the metallic layers includes patterning the undulating shape using photolithography and then wet-etching.

16. The method of claim 10, wherein the at least one of the metallic layers which has an undulating shape is made as a single loop.

17. The method of claim 10, further comprising molding the upper and bottom polymeric layers into a shape matching an adjacent external portion of an eye.

18. The method of claim 10, further comprising using a photoresistant mask to protect the at least one of the metallic layers which has an undulating shape, during subsequent plasma dry etching.

19. The method of claim 1, wherein the at least one of the metallic layers which has an undulating shape is made as a single loop radially spaced inward from a circular periphery of the encapsulating bottom and upper polymer layers.

20. The method of claim 1, further comprising molding the upper and bottom polymeric layers into a shape matching an adjacent external portion of an eye.

21. The method of claim 1, further comprising using a photoresistant mask to protect the at least one of the metallic layers which has an undulating shape, during subsequent plasma dry etching.

22. The method of claim 12, wherein the at least one of the metallic layers which has an undulating shape is made as a single loop.

* * * * *